(12) United States Patent
Wu

(10) Patent No.: US 9,410,183 B2
(45) Date of Patent: Aug. 9, 2016

(54) METHODS AND KITS FOR DETECTION OF O-GLCNAC AND N-GLCNAC MODIFICATION OF PEPTIDES AND PROTEINS

(71) Applicant: RESEARCH AND DIAGNOSTIC SYSTEMS, INC., Minneapolis, MN (US)

(72) Inventor: Zhengliang L. Wu, Edina, MN (US)

(73) Assignee: Bio-Techne Corporation, Minneapolis, MN (US)

( * ) Notice: Subject to any disclaimer, the term of this patent is extended or adjusted under 35 U.S.C. 154(b) by 0 days.

(21) Appl. No.: 14/496,813

(22) Filed: Sep. 25, 2014

(65) Prior Publication Data

US 2015/0087002 A1    Mar. 26, 2015

Related U.S. Application Data

(60) Provisional application No. 61/882,937, filed on Sep. 26, 2013.

(51) Int. Cl.
*C12Q 1/48*    (2006.01)
(52) U.S. Cl.
CPC ........ *C12Q 1/48* (2013.01); *G01N 2333/91102* (2013.01); *G01N 2333/91194* (2013.01); *G01N 2400/00* (2013.01); *G01N 2458/00* (2013.01)
(58) Field of Classification Search
CPC ............. C12Q 1/48; G01N 2333/9119; G01N 2400/00; G01N 2458/00; G01N 2333/911
USPC ......................................................... 435/15
See application file for complete search history.

(56) References Cited

PUBLICATIONS

Vosseller et al. Elevated Nucleocytoplasmic Glycosylation by O-GlcNAc Results in Insulin Resistance Associated With Defects in AKT Activation in 3T3-L1 Adipocytes; PNAS, vol. 99, No. 8 (2002) pp. 5313-5318.*
Skelton et al. Characterization of a Sulfotransferase Responsible for the 4-O-Sulfation of a Terminal Beta-N-Acetyl-D-Galactosamine on Asparagine-Linked Oligosaccharides of Glycoprotein Hormones; The Journal of Biological Chemistry, vol. 266, No. 26 (1991) pp. 17142-17150.*
Graham, F. L., et al., "Characteristics of a Human Cell Line Transformed by DNA from Human Adenovirus Type 5", J. gen. Virol. (1977), pp. 59-72, Issue 36, Great Britain.
Gross, Benjamin J., et al. "Discovery of O-GlcNAc Transferase Inhibitors", J Am Chem Soc, (2005), pp. 14588-14589; Issue 127 (42), The American Chemical Society; JACS Communications, (published online on Sep. 29, 2005); downloaded from http://pubs.acs.org/doi/abs/10.1021/ja0555217 on Dec. 23, 2014.
Leymarie, Marie, et al., "Effective use of mass spectrometry for glycan and glycopeptide structural analysis", Anal Chem., National Institute of Health, Apr. 3, 2012; (available in PMC Apr. 3, 2013) pp. 1-19; Issue 84 (7) 3040-3048.
Matsuura, Aiko, et al., "O-Linked N-Acetylglucosamine Is Present on the Extracellular Domain of Notch Receptors", The Journal of Biological Chemistry, Dec. 19, 2008, pp. 35486-35495, vol. 283, No. 51, The American Society for Biochemistry and Molecular Biology, Inc. Printed in the U.S.A.; downloaded from http://www.jbc.org/ at R&D Systems on Feb. 4, 2015.
Prather, Brittany, et al., "Golgi-resident PAP-specific 3'-phosphatase-coupled sulfotransferase assays", Analytical Biochemistry (2012) pp. 86-92, Issue 423, Elsevier.
Sakaidani, Yuta, et al., "O-linked-N-acetylglucosamine modification of mammalian Notch receptors by an atypical O-GlcNAc transferase Eogt1", Biochemical and Biophysical Research Communications, Mar. 2, 2012, pp. 14-19, Issue 419, (published online Jan. 28, 2012); downloaded from http://www.sciencedirect.com/science/article/pii/S0006291X12001453 on Dec. 23, 2014.
Li, Shan, et al., "Pathogen blocks host death receptor signalling by arginine GlucNAcylation of death domains", Nature, (published online Aug. 18, 2013); pp. 242-246, Issue 501, Macmillan Publishers Limited.
Uchimura, Kenji, et al., "Specificities of N-Acetylglucosamine-6-O-sulfotransferases in Relation to L-selectin Ligand Synthesis and Tumor-associated Enzyme Expression", The Journal of Biological Chemistry, Feb. 8, 2002, pp. 3979-3984, vol. 277, No. 6, The American Society for Biochemistry and Molecular Biology, Inc. Printed in U.S.A., downloaded from http://www.jbc.org/ at R&D Systems on Feb. 4, 2015.
Wu, Zhengliang L., et al., "A versatile polyacrylamide gel electrophoresis based sulfotransferase assay", Biotechnology, Feb. 10, 2010, pp. 1-9, Issue 10:11, BioMed Central (http://www.biomedcentral.com/1472-6750/10/11).
Wu, Zhengliang L., et al., "A new strategy for defining critical functional groups on heparan sulfate", The FASEB Journal, Apr. 2002, pp. 539-545, vol. 16 No. 6; downloaded from http://www.fasebj.org/content/16/6/539.long on Dec. 23, 2014.
Wu, Zhengliang L., et al. "Detecting O-GlcNAc using in vitro sulfation", Glycobiology, Aug. 2014, (published online on May 5, 2014), pp. 740-747, vol. 24, No. 8, Oxford University Press.

* cited by examiner

*Primary Examiner* — Kagnew H Gebreyesus
*Assistant Examiner* — Paul Martin
(74) *Attorney, Agent, or Firm* — Fredrikson & Byron, P.A.

(57) ABSTRACT

Methods and kits for detecting the presence of GlcNAc modification of a peptide or protein. The steps of detection may include combining the peptide or protein with PAP$^{35}$S and a sulfotransferase to produce a reaction product including $^{35}$S labeled GlcNAc modified protein or peptide, removing background labeling with a glycosidase, separating the $^{35}$S labeled GlcNAc modified protein or peptide from PAP$^{35}$S, free S-35 sulfate and labeled oligosaccharides if present, and detecting isotopic emissions from the $^{35}$S labeled GlcNAc modified peptide or protein. The detection may further include, prior to detection, the step of combining the peptide or protein with a GlcNAc transferase and UDP-GlcNAc under appropriate conditions for the GlcNAc transferase to transfer a GlcNAc to the peptide or protein.

12 Claims, 7 Drawing Sheets

METHODS AND KITS FOR DETECTION OF O-GLCNAC AND N-GLCNAC MODIFICATION OF PEPTIDES AND PROTEINS

PRIORITY

The present application claims priority to U.S. Provisional Application No. 61/882,937, filed Sep. 26, 2013, the disclosure of which is hereby incorporated by reference in the entirety.

BACKGROUND

N-acetylglucosamine, often identified as GlcNAc, is a monosaccharide derivative of glucose that modifies proteins of eukaryotic organisms. One form of modification, referred to as O-GlcNAc (O-linked β-N-acetylglucosamine) glycosylation, occurs by the addition of a single N-acetylglucosamine residue to serine/threonine residues. This modification was long thought to exist solely on nuclear and cytosolic proteins, but it has been recently discovered on extracellular proteins. Unlike other types of glycosylation, the sugar residue is not elongated into complex oligosaccharides. In fact, O-GlcNAc glycosylation shares many features with protein phosphorylation, a fundamental mechanism for intracellular communication, and it has been postulated that O-GlcNAc glycosylation has a mutually exclusive relationship with phosphorylation. O-GlcNAc glycosylation is involved in many cellular processes such as nutrient sensing, stress response, transcription, translation, cell signaling and cell cycle regulation. O-GlcNAc glycosylation is also involved in many human diseases including diabetes, Alzheimer's disease and cancer.

An alternative form of GlcNAc glycosylation, N-GlcNAc (N-linked β-N-acetylglucosamine) glycosylation, is also known. N-GlcNAc modification of proteins occurs on arginine residues and has been observed in bacteria, for example.

Despite the importance of GlcNAc glycosylation, detection of GlcNAc glycosylation is a challenging task. O-GlcNAc glycosylation has no effect on protein mobility during electrophoresis because of its small size and neutral charge. Traditionally, antibodies and lectins have been applied to detect O-GlcNAc, but these reagents suffer from weak binding affinity and limited specificity for O-GlcNAc. Recently, methods for labeling O-GlcNAc with radioisotope tagged or chemically modified galactose using recombinant galactosyltransferases have been reported. For example, $^3$H tagged galactose, Keto-Gal, or GalNAz were covalently linked to O-GlcNAc using galactosyltransferases or mutant galactosyltransferase Gal-T1 (Y289L). However, detection of O-GlcNAc glycosylation remains difficult. Chemoenzymatic labeling with mutant galactosyltransferase Gal-T1 (Y289L) has also been applied to detect N-GlcNAc. In addition, mass spectrometry has been applied to detect GlcNAc modification in general.

SUMMARY

Various embodiments include kits and methods for detecting and quantifying GlcNAc modification of peptides and proteins, including O-GlcNAc and N-GlcNAc modification. In one embodiment, the method of detecting the presence of GlcNAc modification of a peptide or protein includes combining the peptide or protein with PAP$^{35}$S and CHST2 or CHST4 to produce a reaction product including $^{35}$S labeled GlcNAc modified protein or peptide, removing background labeling with a glycosidase, separating the $^{35}$S labeled GlcNAc modified protein or peptide from PAP$^{35}$S, free S-35 sulfate and labeled oligosaccharides, and detecting isotopic emissions from the $^{35}$S labeled GlcNAc modified peptide or protein.

In another embodiment, the method includes detecting GlcNAc modification of a peptide or protein including combining the peptide or protein with a GlcNAc transferase and UDP-GlcNAc under appropriate conditions for the transferase to transfer a GlcNAc to the peptide or protein to produce a first reaction product, combining the first reaction product with PAP$^{35}$S and CHST2 and/or CHST4 under appropriate conditions for the CHST2 and/or CHST4 to cause sulfation of any GlcNAc present on the peptide or protein with $^{35}$S, removing background labeling with glycosidases, separating the $^{35}$S labeled GlcNAc modified protein or peptide from PAP$^{35}$S, free S-35 sulfate and labeled oligosaccharides, and detecting isotopic emissions from the $^{35}$S labeled GlcNAc modified peptide or protein.

In some embodiments, the method is for the detection of O-GlcNAc modification. The method may further include combining the peptide or protein with EOGT or OGT and UDP-GlcNAc, and may still further include combining the peptide or protein with CD39L3 at the same time as combining the peptide or protein with EOGT or OGT and UDP-GlcNAc. The method may include the use of IMPAD1. In some embodiments, the method includes resolving the reaction product in gel using gel electrophoresis and may further include producing a radiograph of the gel and identifying a band corresponding to O-GlcNAc or N-GlcNAc modified peptide or protein, or scanning the radiograph and detecting the density of a band corresponding to the $^{35}$S labeled GlcNAc modified protein. In other embodiments, the method includes detecting isotopic emissions from the gel using a phosphorimager. In some embodiments, it includes passing the reaction product through a desalting column, applying the reaction product to a filter having an affinity for protein or peptide, or binding the $^{35}$S labeled GlcNAc modified protein or peptide using antibody specific to the protein or peptide, forming an immunoprecipitate, and separating out the immunoprecipitate. Such methods may further include counting radioactive emission of the $^{35}$S labeled GlcNAc modified protein or peptide using a liquid scintillation counter. The method may also include the use of a glycosidase such as PNGase F.

Another embodiment is a kit for detecting the presence of O-GlcNAc modification of a peptide or protein including CHST2 and/or CHST4 and PAP$^{35}$S or a PAPS synthesis kit which may include PAPS Enzyme Mix and PAPS Substrate Mix. The kit may further include EOGT or OGT, and may also further include UDP-GlcNAc. In some embodiments it also may include CD39L3 and/or IMPAD1. The kit may further include a buffer. In some embodiments, the kit may include a glycosidase, such as PNGase F or O-GlcNAcase (OGA). The kit may also include instructions for synthesizing PAP$^{35}$S and for reacting the PAP$^{35}$S with the CHST2 and/or CHST4 and for deglycosylation with OGA and for deglycosylation with PNGase F and for detecting $^{35}$S sulfation of the peptide or protein.

In another embodiment, the kit for detecting the presence of O-GlcNAc modification of a peptide or protein includes EOGT or OGT, UDP-GlcNAc, OGA, PNGase F, CHST2 and/or CHST4, PAP$^{35}$S or a PAP synthesis kit which may include PAPS Enzyme Mix and PAPS Substrate Mix, and may also include instructions for reacting PAP$^{35}$S with the CHST2 and/or CHST4 and for deglycosylation with OGA and for deglycosylation with PNGase F and for detecting $^{35}$S sulfation of the O-GlcNAc modified peptide or protein. Such a kit may further include CD39L3, IMPAD1, and/or a buffer.

BRIEF DESCRIPTION OF THE FIGURES

The following drawings are illustrative and therefore do not limit the scope of the invention. The drawings are not to scale (unless so stated) and are intended for use in conjunction with the explanations in the following detailed description.

DETAILED DESCRIPTION

For the purpose of promoting an understanding of the principles of the invention, various embodiments will now be described. It will, nevertheless, be understood that no limitation of the scope of the invention is thereby intended; any alterations and further modifications of the described or illustrated embodiments, and any further applications of the principles of the invention as illustrated therein, are contemplated as would normally occur to one skilled in the art to which the invention relates.

Various embodiments described herein detect O-GlcNAc or N-GlcNAc glycosylation through the use of sulfation of the O-GlcNAc or N-GlcNAc with $^{35}S$. The radioactive decay of the isotope $^{35}S$ can be detected and used to identify the presence of O-GlcNAc or N-GlcNAc glycosylation in a sample, such as through the use of SDS gel electrophoresis and autoradiography or a phosphorimager, or though scintillation counting.

Figure 1:
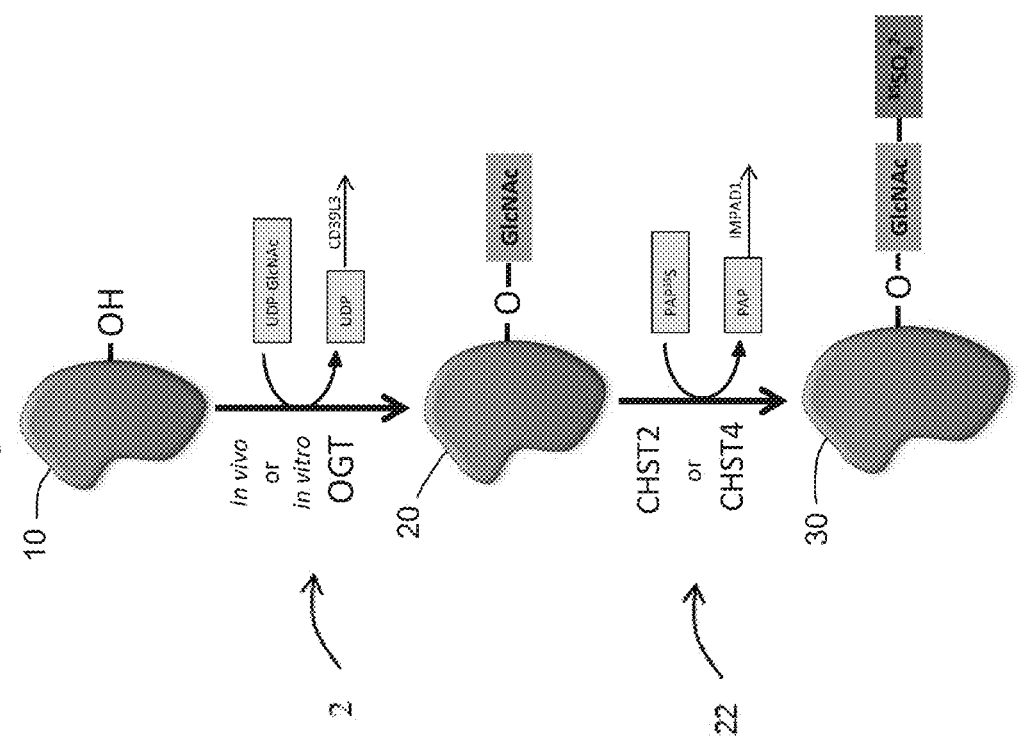
FIG. 1 is a schematic diagram representing O-GlcNAc modification of a peptide or protein and labeling by sulfation.

FIG. 1 is a schematic diagram of a two-step reaction for O-GlcNAc detection which may be used in various embodiments. A protein 10, or alternatively a peptide, which is capable of O-GlcNAc modification is shown. The protein 10 includes a hydroxyl group as shown, which is provided by a serine or threonine residue. In a first reaction 2, O-GlcNAc transferase (OGT) catalyzes the transfer of GlcNAc from UDP-GlcNAc (Uridine 5'-diphospho-N-acetylglucosamine) to the protein 10 to form an O-GlcNAc glycosylated protein 20 and UDP (uridine diphosphate) which is hydrolyzed by CD39L3. This first reaction 2 may occur in vivo through the inherent process of O-GlcNAc glycosylation, or may be created in vitro.

Alternatively (not shown), when the method is used for detection of N-GlcNAc modification, the first step includes a protein (or peptide) having a guanidine group provided by an arginine residue. In this first reaction, an arginine specific GlcNAc transferase, such as NleB from pathogenic E. coli or Salmonella as described by Sun L. et al, Nature 2013 (501): 242-246, catalyzes the transfer of GlcNAc from UDP-GlcNAc to the protein to form an N-GlcNAc glycosylated protein, with UDP remaining as a product. As with O-GlcNAc glycosylation, N-GlcNAc glycosylation may occur inherently in vivo or may be created in vitro.

In a second reaction 22, one or more GlcNAc specific sulfotransferases catalyze the sulfation of O-GlcNAc on the O-GlcNAc modified protein 20. The source of sulfate for this reaction is PAPS (3'-Phosphoadenosine-5'-phosphosulfate), which is the universal sulfate donor for sulfotransferases, resulting in PAP (3'-Phosphoadenosine-5'-phosphate). However, the PAPS used in embodiments of the invention includes isotopic sulfur, $^{35}S$, and is therefore identified herein as $PAP^{35}S$. The sulfated O-GlcNAc glycosylated protein 30 that results from this reaction therefore includes $^{35}S$, such that the sulfate group can act as a radio-label on the O-GlcNAc of the modified protein. This radio-label may be detected to identify a protein as having been O-GlcNAc glycosylated. Alternatively (not shown), when the method is used for detection of N-GlcNAc modification of the protein, the same second reaction 22 may be used to form a $^{35}S$ labeled N-GlcNAc modified protein.

In some embodiments, the method is performed in two steps, with the O-GlcNAc or N-GlcNAc glycosylation reaction first, followed by the $^{35}S$ sulfation reaction. The components of each reaction may be combined separately in a two-step process, or alternatively the components of both of these reactions could be combined at the same time, in a single step, and the two step reaction process would occur within the sample. In some embodiments, the O-GlcNAc or N-GlcNAc glycosylation of the protein may have occurred in vivo. In such embodiments, the in vitro glycosylation step may not be necessary and the method may only include the $^{35}S$ sulfation step.

There are numerous naturally occurring peptides and proteins which may be O-GlcNAc or N-GlcNAc glycosylated and any of these may be sulfated for detection of the O-GlcNAc or N-GlcNAc moiety according to embodiments described herein. In addition, synthetic peptides which may be O-GlcNAc or N-GlcNAc glycosylated may likewise be sulfated to detect the O-GlcNAc or N-GlcNAc moiety according to the methods described herein.

In some embodiments, the O-GlcNAc or N-GlcNAc glycosylation of a protein or peptide may occur in vivo. In other embodiments, the O-GlcNAc or N-GlcNAc glycosylation of a protein or peptide may be performed in vitro through the use of O-GlcNAc transferase (OGT) and/or extracellular O-GlcNAc transferase (EOGT) or an arginine specific GlcNAc transferase. These transferases catalyze the transfer of GlcNAc from UDP-GlcNAc to the protein or peptide, leaving behind UDP.

In some embodiments, a phosphatase active on UDP, such as ectonucleoside triphosphate diphosphohydrolase-3, also known as CD39L3 or NTPDase-3, may optionally be added to the O-GlcNAc or N-GlcNAc glycosylation reaction. The phosphatase hydrolyzes UDP, thereby removing it to prevent inhibition of O-GlcNAc glycosylation by OGT and/or EOGT or N-GlcNAc glycosylation by the arginine specific GlcNAc transferase, thereby helping to drive more complete O-GlcNAc or N-GlcNAc glycosylation.

Once the peptide or protein has been O-GlcNAc or N-GlcNAc glycosylated, the presence of the O-GlcNAc or N-GlcNAc moiety may be detected using the sulfation reaction. Sulfotransferases which may be used for this reaction include GlcNAc-specific sulfotransferases, N-acetylglucosamine 6-O-sulfotransferase 1 (CHST2) and N-acetylglucosamine 6-O-sulfotransferase 2 (CHST4). Both enzymes introduce a sulfate to the 6-0 of the non-reducing N-acetyl-glucosamine (GlcNAc) residues within various glycan structures. Either one or the other or both of the sulfotransferases may be used. The O-GlcNAc or N-GlcNAc on some peptides or proteins may be more completely sulfated using one sulfotransferase or the other, and therefore selection of the sulfotransferase may be made on that basis, if known. However, if the effectiveness of the sulfotransferases on a particular protein or peptide is unknown, it may be preferable to use both CHST2 and CHST4 in combination.

In some embodiments, it may be preferable to use CHST4 because, as described further in the experimental section, in some reactions the use of CHST2 resulted in self-labeling (sulfation of CHST2 itself) such that the CHST2 became labeled with $^{35}S$. Such self-labeling was not observed with CHST4. However, if CHST2 is first deglycosylated, this self-labeling of CHST2 can be avoided. Therefore, depending upon the conditions of the reaction, either CHST2 or CHST4 or both may be used. In some embodiments, the method may include a step of deglycosylation of the sulfotransferase, such as CHST2, prior to use of the sulfotransferase in the sulfation reaction, or the use of a deglycosylated sulfotransferase in the sulfation reaction. For example, the sulfotransferase may be deglycosylated by incubating it with PNGase F.

The PAP$^{35}$S used in various embodiments may be purchased commercially from radiochemical vendors such as PerkinElmer or American Radiolabeled Chemical. Alternatively, the PAP$^{35}$S may be created, such as by using the PAPS synthesis kit available from R & D Systems of Minneapolis, Minn. For example, PAP$^{35}$S may be synthesized from ATP through two steps. In the first step, adenosine triphosphate (ATP) is converted to adenosine-5'-phosphosulfate (APS) by ATP sulfurylase in the presence of $^{35}S$, and pyrophosphate (PPi) is generated as a byproduct. In the second step, the APS is converted to PAPS by APS kinase and adenosine diphosphate (ADP) is generated as a byproduct. To drive the reaction forward, the pyrophosphate can be further degraded to phosphate (Pi) by adding inorganic pyrophosphatase to the first reaction to eliminate feedback inhibition, and the ADP can be converted back to ATP using pyruvate kinase.

In some embodiments, a phosphatase active on PAP may optionally be added to the sulfation reaction. An example of an appropriate phosphatase is inositol monophosphatase 3 (IMPAD1). The phosphatase such as IMPAD1 removes the PAP, hydrolyzing the PAP to AMP (adenosine monophosphate) thereby preventing feedback inhibition of CHST2 and/or CHST4 and driving the sulfation reaction forward.

Once the O-GlcNAc glycosylated protein has been sulfated with a $^{35}S$ sulfate group, the presence of the radio-label can be detected. For example, in some embodiments, the reaction mixture may be resolved using electrophoresis, such as by using polyacrylamide gel electrophoresis using sodium dodecyl sulfate (SDS PAGE). An X-ray film may then be placed on or in proximity to the gel and allowed to develop. Decay of the isotope will cause bands to appear on the autoradiographic image. The size of the bands can be quantified, such as by scanning the image using a scanner and calculating the size and/or density (intensity) of the bands using densitometry analysis software. The size and density of the bands correlates to the amount of radioisotope present in the band.

Alternatively, after separation of the sample using SDS PAGE, the gel may be analyzed using a phosphorimager. The phosphorimager can directly detect and quantify the radioactive label present in the bands of the gel. An example of such a phosphorimager is the Amersham Molecular Devices Storm 820.

In order to identify any bands due to excess PAP$^{35}$S or free $^{35}SO_4$, the PAP$^{35}$S may be run alone on the same gel at the same time as the reaction samples to function as a control. In this way, bands present on the PAP$^{35}$S only control lane may be identified as not corresponding to O-GlcNAc or N-GlcNAc. The corresponding bands present in any test lanes (having migrated the same distance) can therefore be ignored as being caused by sources of signal other than an O-GlcNAc or N-GlcNAc glycosylated protein or peptide. In some cases, the sulfotransferase may sulfate itself, resulting in self-labeling. Therefore, a sample that contains the sulfotransferase and PAP$^{35}$S (but no protein, peptide, or UDP-GlcNAc) may be prepared and electrophoresed in the gel, along with the test sample, as a control in order to identify bands corresponding to sulfotransferase self-labeling. Any bands representing self-labeling (having migrated the same distance as the control bands) can be disregarded in the test lane. In this way, self-labeled sulfotransferase can be identified and disregarded in the test lanes such that it is not incorrectly identified as representing an O-GlcNAc or N-GlcNAc glycosylated peptide or protein of interest.

In other embodiments, the method includes detection of $^{35}S$ labeling of the O-GlcNAc or N-GlcNAc glycosylated protein or peptide through the use of liquid scintillation counting. In such embodiments, the sample may be processed to remove background signal, such as any remaining free PAP$^{35}$S and free $^{35}S$, after the labeling reaction. This may be done by passing the sample through a desalting column, for example. The radiation of the sample may then be counted using a scintillation counter. Alternatively, the reaction mixture may be spotted on a filter disc that has an affinity for the protein or peptide. The filter disk may then be washed to remove any unbound or loosely bound PAP$^{35}$S and free $^{35}S$, such as by using a buffer and/or ethanol. The radiation of the disc may then be counted using a scintillation counter. After removal of the background signal, the reaction sample or filter may be placed into a liquid scintillation counter and the instrument may be directed to measure and report the amount of radiation.

Various embodiments may be used to detect O-GlcNAc or N-GlcNAc glycosylation of proteins or peptides. For example, various embodiments may be used to detect O-GlcNAc glycosylation states of insulin signaling proteins, which may be elevated in diabetic patients. For example, the level of O-GlcNAc glycosylation of insulin signaling proteins in vivo may be analyzed at various times points, such as before and after a change or over time, in order to evaluate the effect of lifestyle or medication changes of O-GlcNAc glycosylation, or as a component of disease monitoring. The state of O-GlcNAc glycosylation may also be studied in vivo in other diseases such as on tau proteins in Alzheimer's disease. For example, the in vivo O-GlcNAc glycosylation state of tau protein may be monitored in individual patients across time for disease monitoring or for monitoring the effectiveness of a therapy.

In some embodiments, the method may be used to detect the effect of an agent, such as a potential pharmaceutical agent, upon O-GlcNAc or N-GlcNAc glycosylation of a protein or peptide. For example, the agent may be combined with the protein or peptide before or at the same time as the O-GlcNAc or N-GlcNAc glycosylation reaction (that is, before or at the same time as the reaction of the OGT or EOGT or arginine GlcNAc transferase and the UDP-GlcNAc with the protein or peptide). The sample may then be sulfated using the sulfotransferases and PAP$^{35}$S as described above, and the amount of sulfation may be detected and used as an indication of the extent of O-GlcNAc or N-GlcNAc glycosylation. In some embodiments, a control reaction may be performed in which the protein or peptide undergoes the same reactions but without exposure to the agent. The results may then be compared to determine whether the agent caused increased or decreased O-GlcNAc or N-GlcNAc glycosylation or had no effect. Alternatively, the results for a reaction including one agent may be compared to the results for a reaction including another agent, to compare the effects of various agents upon O-GlcNAc or N-GlcNAc glycosylation to each other.

Some embodiments may be used to study phosphorylation of a protein or peptide, such as by making use of the mutual exclusivity between O-GlcNAc modification and phosphorylation that may exist for a protein or peptide. For example, the effect of an agent on phosphorylation may be analyzed using this method by measuring the level of O-GlcNAc modification. In such cases, a reduction in O-GlcNAc modification may indicate an increase in phosphorylation, and vice versa.

Various embodiments include kits for the detection of O-GlcNAc or N-GlcNAc glycosylation of a protein or peptide. In some embodiments, the kit includes a sulfotransferase, such as either CHST2 or CHST4 or both CHST2 and CHST4. A kit for detection of O-GlcNAc glycosylation may further include OGT or EOGT or both OGT and EOGT. A kit for detection of O-GlcNAc glycosylation may further include OGA. A kit for detection of N-GlcNAc glycosylation may further include an arginine GlcNAc transferase.

In some embodiments the kit includes a sulfotransferase, such as CHST2 and/or CHST4, and either $PAP^{35}S$ or a $PAP^{35}S$ synthesis kit. The kit may further include one or more transferases (OGT and/or EOGT or an arginine GlcNAc transferase) and may also include a phosphatase that is specific for UDP.

The kit may further include instructions for the sulfation of the protein or peptide being assayed for O-GlcNAc glycosylation using the sulfotransferase and $PAP^{35}S$, which may or may not be provided as part of the kit. In some embodiments, the kit includes $PAP^{35}S$ or a $PAP^{35}S$ synthesis kit. In some embodiments, the $PAP^{35}S$ synthesis kit may include a PAPS Enzyme Mix and a PAPS Substrate Mix. The PAPS Enzyme Mix may include a buffer such as a Tris buffer with glycerol, ATP sulfurylase, APS kinase, inorganic pyrophosphatase, and pyruvate kinase. The PAPS Substrate Mix may include ATP, phosphoenolpyruvate and enzyme co-factors. The $PAP^{35}S$ synthesis kit may further include a gel loading dye, such as a 6× gel loading dye including Tris buffer with glycerol and bromophenol blue, and a PAPS storage buffer, which may be a Tris buffer. Alternatively, users of the kit may obtain the $^{35}S$ sulfate separately to use with the $PAP^{35}S$ synthesis kit.

In some embodiments the kit may include a sulfotransferase such as CHST2 and/or CHST4, and OGT and/or EOGT, as well as an apyrase that is specific for UDP such as CD39L3. The kit may further include either $PAP^{35}S$ or a $PAP^{35}S$ synthesis kit as described above. The kit may also further include IMPAD1. In some embodiments, the kit may also include UDP-GlcNAc.

Kits for the detection of O-GlcNAc or N-GlcNAc glycosylation of a protein or peptide may further include instructions for using the kit. For example, the instructions may include combining the protein or peptide with the transferase(s) included in the kit (OGT and/or EOGT or the arginine GlcNAc transferase) and UDP-GlcNAc and optionally with CD39L3 if it is included in the kit, for carrying out the O-GlcNAc glycosylation reaction. It may further include instructions for next combining the protein or peptide with CHST2 and/or CHST4 and $PAP^{35}S$, and optionally with IMPAD1 if it is included in the kit, for carrying out the sulfation reaction. Alternatively, the instructions may direct the user to combine the protein or peptide with all of the components of the reaction at once, rather than in two separate steps, to perform a combined reaction.

Various embodiments include methods of detecting O-GlcNAc or N-GlcNAc glycosylation of a protein or peptide of interest. In some embodiments, the method may include combining the protein or peptide with the transferase (OGT and/or EOGT or arginine GlcNAc transferase) and UDP-GlcNAc to form a first reaction mixture under appropriate conditions and using sufficient quantities of the components for the O-GlcNAc glycosylation to occur. The reaction may be performed in a buffer solution, such as at a pH from about 7.0 to 8.0 and about 0.5 mM to about 20 mM $Mn^{2+}$. An example of an appropriate buffer is a Tris buffer, such as 25 mM Tris, 0.15 M NaCl, 10 mM $Mn^{2+}$ buffer at pH 7.5. The method may also include combining CD39L3 with the first reaction mixture in sufficient quantities to reduce or prevent feedback inhibition of the OGT or EOGT. Next, the first reaction mixture may be combined with either CHST2 and CHST4 or both and $PAP^{35}S$ to form a second reaction mixture, under appropriate conditions and using sufficient quantities of the components for sulfation of the O-GlcNAc to occur. This reaction may preferably be performed in a buffer solution, such as at pH of about 7.0 to about 8.0. An example of an appropriate buffer is a Tris buffer, such as 100 mM Tris, 150 mM NaCl buffer at a pH of 7.5. The method may further include combining IMPAD1 with the second reaction mixture in sufficient quantities to prevent or reduce feedback inhibition of the CHST2 and/or CHST4.

Alternatively, the O-GlcNAc or N-GlcNAc glycosylation may occur in the same reaction mixture as the O-GlcNAc or N-GlcNAc sulfation. In such embodiments, the method may include combining the protein or peptide with the transferase(s) (OGT and/or EOGT or arginine GlcNAc transferase), UDP-GlcNAc, CHST2 and/or CHST4, and $PAP^{35}S$ at the same time, under appropriate conditions and in sufficient amounts of the components for both the GlcNAc glycosylation reaction and the sulfation reaction to occur. The method may further include combining CD39L3 and/or IMPAD1 with the other components in the reaction mixture.

Once the O-GlcNAc or N-GlcNAc glycosylation and sulfation reactions are complete, the method may further include detection of $^{35}S$ in the product. This may be accomplished by various methods such as through the use of SDS-PAGE electrophoresis. In such embodiments, detection of $^{35}S$ includes preparing the sample, such as by the addition of a loading dye. Next, the method includes loading the prepared sample into a sample well of the separating gel and applying a voltage to the gel, according to known methods, for sufficient time to separate the components of the product into various bands based upon molecular weight. Once the separation step is done, the method includes drying the gel, applying an X-ray film to the gel, or in proximity to the gel, for sufficient time for the $^{35}S$ present in various protein bands to expose the X-ray film. An exposure line indicates the presence of $^{35}S$ in the band. The X-ray film, or an autoradiograph thereof, may then be used to determine whether the band represents the protein of interest.

In some embodiments, the method including SDS-PAGE may further include preparing a sample including only $PAP^{35}S$ as a control. In some embodiments, the method further includes preparing a sample including only $PAP^{35}S$ and the sulfotransferase(s) used in the test reaction as a control. In some embodiments, both $PAP^{35}S$ alone, and $PAP^{35}S$ and the sulfotransferase(s) may be used as controls. The method further includes loading one or more controls into different wells of the same separation gel as the product and applying the voltage and the X-ray film as described above. The method may further include interpreting the results on the X-ray film or autoradiograph, which may include ignoring or disregarding any bands of the product which are also present in the controls, as these bands do not represent the O-GlcNAc or N-GlcNAc glycosylated protein, and identifying the remaining band as corresponding to the sulfated O-GlcNAc or N-GlcNAc glycosylated protein, if present. If no O-GlcNAc or N-GlcNAc glycosylation of the test protein or peptide occurred, then there will be no resulting labeled band on the gel (that is, there will be no band which does not correspond to a band in the control or controls).

In some embodiments, the method of detecting O-GlcNAc or N-GlcNAc glycosylation may further include the use of a glycosidase to remove any labeled N-glycans from the protein or peptide. Such a glycosidase is preferably specific for N-glycans, without effecting O-glycans. An example of such a glycosidase is PNGase F. The N-glycan specific glycosidase can be added to the sample after the O-GlcNAc glycosylation reaction, such as before labeling with PAP$^{35}$S, during the PAP$^{35}$S labeling step, or after the PAP$^{35}$S labeling step. However, if it is used, the N-glycan specific glycosidase should be used before the sample is separated on the gel and before counting with a scintillation counter. For example, the step of N-deglycosylation on CHST2 can be performed by directly incubating CHST2 with PNGase F at a 5 to 1 mass ratio in Tris buffer at pH 7.5. In some embodiments, an N-glycan specific glycosidase such as PNGase-F may be included with the O-GlcNAc detection kit.

In some embodiments, the method of detecting O-GlcNAc or N-GlcNAc glycosylation may further include the use of a glycosidase to remove existing O-GlcNAc or N-GlcNAc from a sample and abolish the labeling by CHST2 and/or CHST4, which confirms that the labeling is on O-GlcNAc or N-GlcNAc. For example, OGA can be used to remove O-GlcNAc and may be included with the O-GlcNAc detection kit.

In some embodiments, the O-GlcNAc or N-GlcNAc glycosylation occurs in vivo. In some such embodiments, the O-GlcNAc or N-GlcNAc modified protein or peptide may be sulfated according to various embodiments after it is extracted from the cell. Extraction of the protein or peptide may be performed in a variety of ways. For example, the cells may be lysed first under mild detergent conditions to rupture the cells but not the nuclei and then centrifuged to obtain the components of the cytoplasm in the supernatant. The pellet including the nuclei may then be subjected to more stringent conditions to rupture the nuclei, and then centrifugation may be performed to separate the nuclear components into the supernatant. More specifically, a quantity of cells may be collected, such as about $1 \times 10^7$ cells. The cells may then be washed one or more times. In some embodiments, the cells may be washed first with phosphate buffered saline and then with an isotonic lysis buffer, such as 10 mM Tris-HCl, 2 mM $MgCl_2$, 3 mM $CaCl_2$, 0.3 M sucrose, 0.2 mM phenylmethylsulfonyl fluoride, and 0.5 mM dithiothreitol. The washed cells may then be suspended, such as in 150 µL of the isotonic lysis buffer, and processed to lyse the cells. This may be accomplished by passing the cell suspension slowly through a syringe multiple times, such as through a 27 gauge needle 6 times. The lysate may then be separated by centrifugation to produce a supernatant which is the cytoplasmic extract. For example, the lysate may be centrifuged for 20 minutes at 11,000×g. The pellet may be further processed to produce a nuclear extract. For example, the pellet may be suspended in an extraction buffer which is hypertonic such as 10 mM HEPES, pH 7.9, 1.5 mM $MgCl_2$, 0.2 mM EDTA, 25% glycerol, 0.42 M NaCl, 0.2 mM PMSF, and 0.5 mM DTT and then centrifuged again with the nuclear extract being the supernatant. The cytoplasmic extracts and nuclear extracts produced in this way may be used as the source of protein for sulfation of the GlcNAc according to the embodiments described herein.

In other embodiments, if the protein or peptide of interest is known, an immunoprecipitation reaction targeted to the protein or peptide may be used to capture and isolate the in vivo or in vitro O-GlcNAc or N-GlcNAc modified protein.

EXPERIMENTAL

In each of the following examples, the components were obtained or created as described in this paragraph. 3'-Phosphoadenosine-5'-phosphosulfate (PAPS), PAP$^{34}$S, Endo F1, Endo H, EndoF3, PNGase F, recombinant *B. thetaiotaomicron* O-GlcNAcase (OGA), recombinant human CHST2, CHST4, CD39L3 and recombinant mouse IMPAD1 were from R&D Systems (Minneapolis, Minn.). Mouse EOGT from amino acid 23 to 523 (as described by Sakaidani, Y., et al. (2012)), 'O-linked-N-acetylglucosamine modification of mammalian Notch receptors by an atypical O-GlcNAc transferase Eogt1', *Biochem Biophys Res Commun*, 419 (1), 14-9 was expressed with a C-terminal 6×His tag in NS0 cells. Human OGT from amino acid 382 to 1046 was cloned and expressed in *E. coli* as previously described with a C-terminal His tag according to the method described by Gross et al. (2005), 'Discovery of O-GlcNAc transferase inhibitors', *J Am Chem Soc*, 127 (42), 14588-9. The EGF20 of *Drosophila* Notch receptor from amino acid 791 to 829 was cloned as previously described (Matsuura et al. 2008) and expressed in *E. coli*. Recombinant OGT, EOGT and EGF20 were purified using nickel-affinity and gel filtration chromatography. The lysates of OGT and EGF20 expression cells or conditioned medium of EOGT expression was first loaded onto a 20 mL nickel affinity column with an ÄKTA™ (GE Healthcare) prime and the bound proteins were then eluted with 200 mL each of 0.1 M and 0.5 M imidazole solution at pH 6.5. The nickel-purified proteins were further separated on a 450 mL Superdex™-200 gel filtration column with an ÄKTA FPLC system in 25 mM Tris, 150 mM NaCl, pH 7.5. PAP$^{35}$S was synthesized from carrier-free $Na_2^{35}SO_4$ (43 Ci/mg, from American Radiolabeled Chemicals, Inc.) as previously described by Wu, Z. L., et al. (2002), 'A new strategy for defining critical functional groups on heparin sulfate', FASEB J, 16 (6), 539-45. O-GlcNAc peptide (catalogue number C33374) and Phosphopeptide (catalogue number C33373) that had identical amino acid sequences which were modified on Ser5 by O-GlcNAcylation and phosphorylation, respectively, were from Invitrogen. GlcNAc and UDP-GlcNAc were from Sigma Aldrich.

Figure 6:
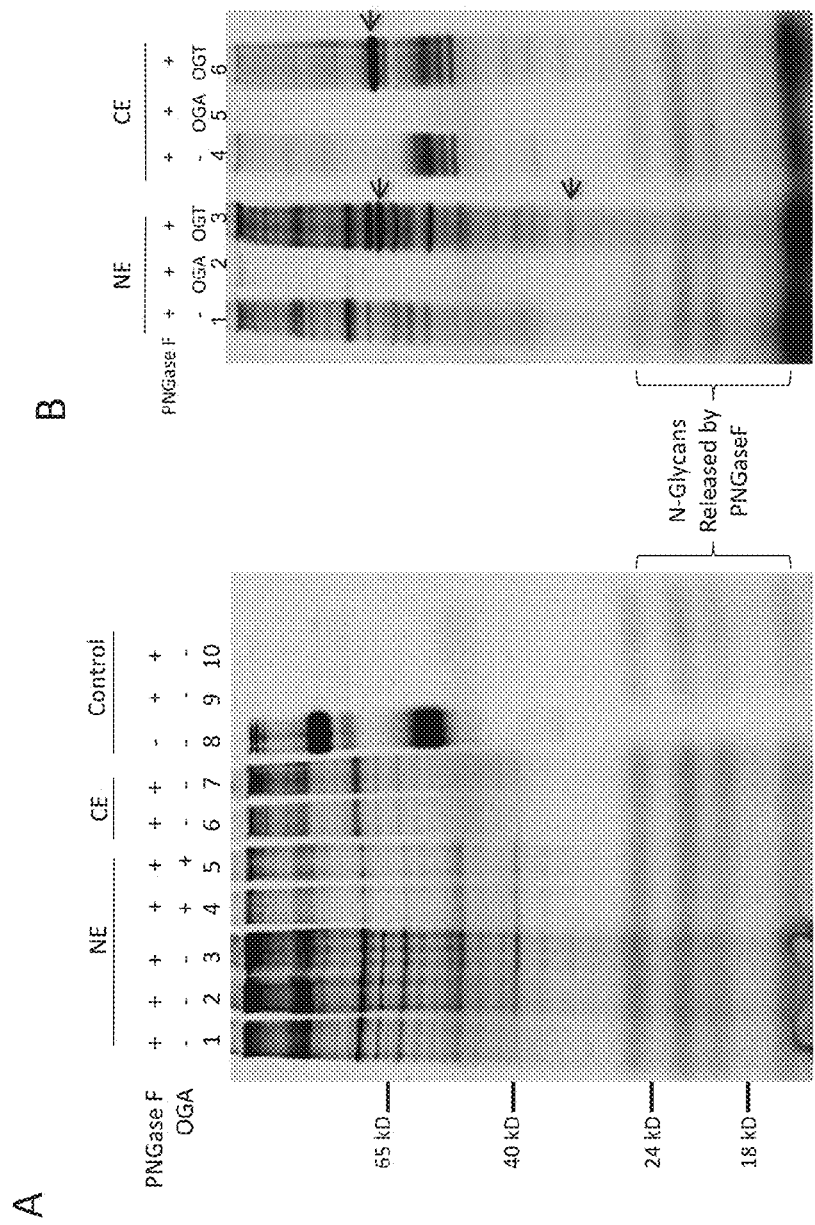
FIGS. 6A and 6B are autoradiographic images of samples resolved by gel electrophoresis showing $^{35}S$ sulfation of nuclear and cytoplasmic extracts by CHST2.
Figure 7:
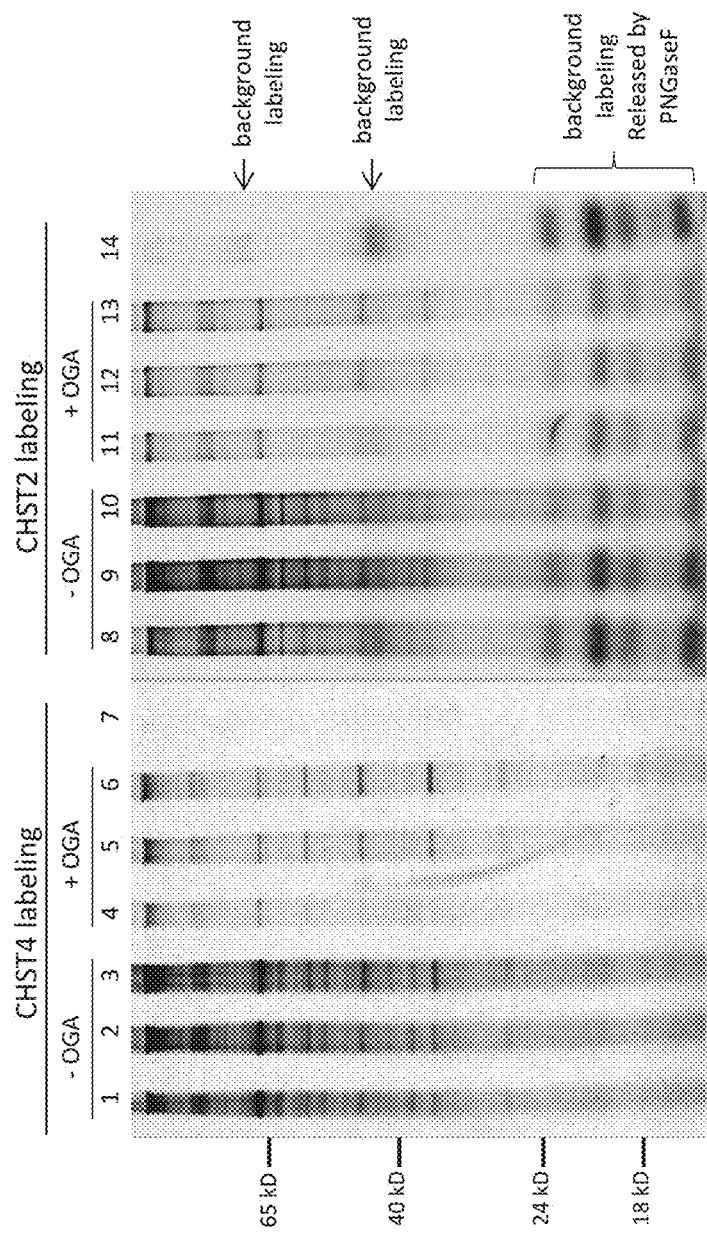
FIG. 7 is an autoradiographic image of samples resolved by gel electrophoresis showing $^{35}S$ sulfation of nuclear extracts, with or without prior OGA treatment, by CHST2 and CHST4.

For a typical sulfotransferase labeling reaction in the following examples, a sample of 5 µL was mixed with 5 µL of PAP$^{35}$S (>$10^7$ CPM) and 0.5 µg of CHST2 or CHST4 in a reaction buffer containing 100 mM Tris, 150 mM NaCl at pH 7.5. Reactions were incubated at 37° C. for at least 20 minutes and then stopped with 5 µL SDS stop/loading buffer (100 mM Tris, 10% SDS, 30% glycerol, 60 mM β-mercaptoethanol, and 0.01% bromophenol blue, pH 8.0). In examples 5 and 6 (the results of which are shown in FIGS. 6 and 7), a higher input of PAP$^{35}$S and longer reaction time was applied to increase the signals for detection. For N-deglycosylation, the completed labeling reaction as described above was further treated with 0.2 µg of PNGase F or Endo F3 and incubated at 37° C. for an additional 20 minutes.

Figure 2:
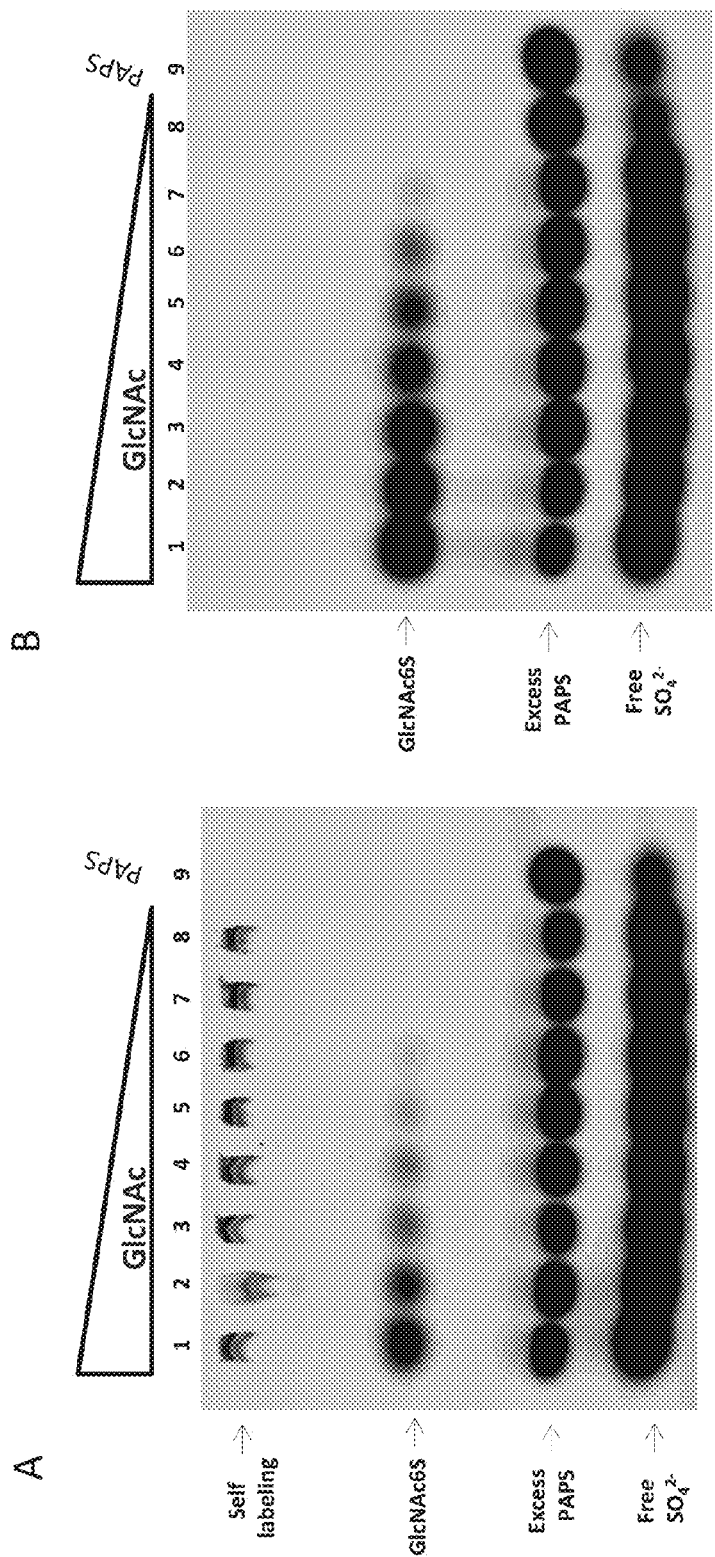
FIGS. 2A and 2B are autoradiographic images of samples resolved by gel electrophoresis showing $^{35}S$ sulfation of GlcNAc by CHST2 (FIG. 2A) and CHST4 (FIG. 2B).
Figure 3:
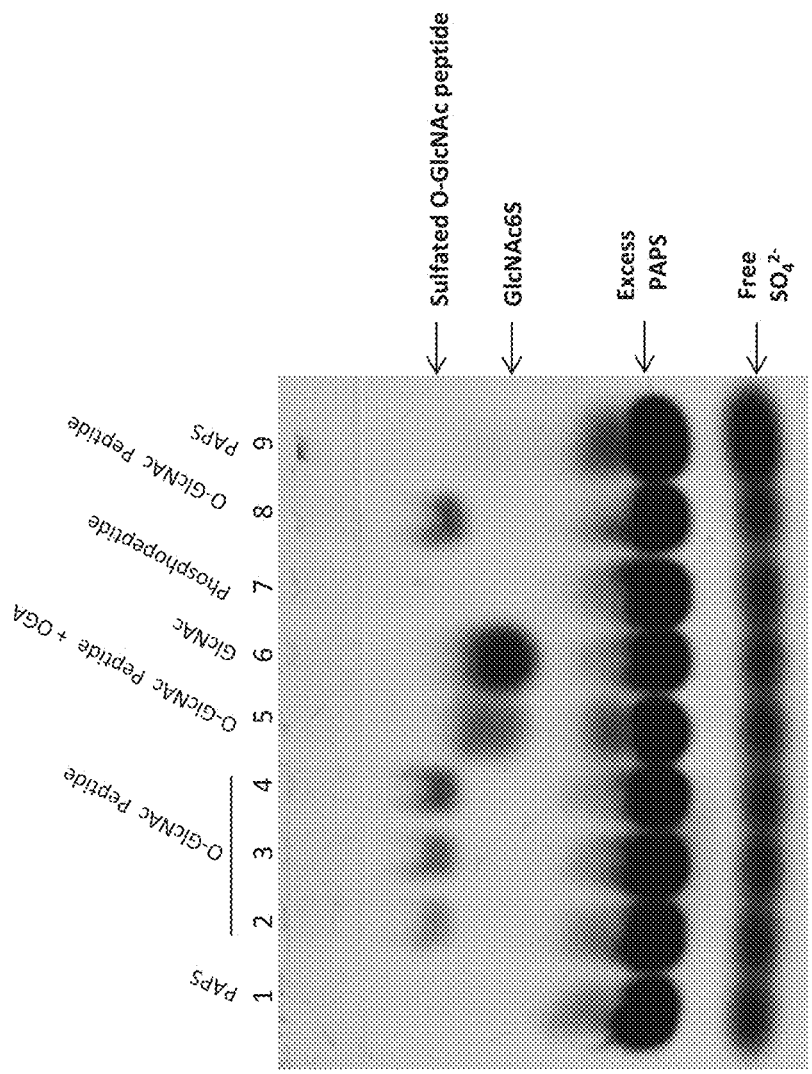
FIG. 3 is an autoradiographic image of samples resolved by gel electrophoresis showing $^{35}S$ sulfation of O-GlcNAc peptide by CHST4.
Figure 5:
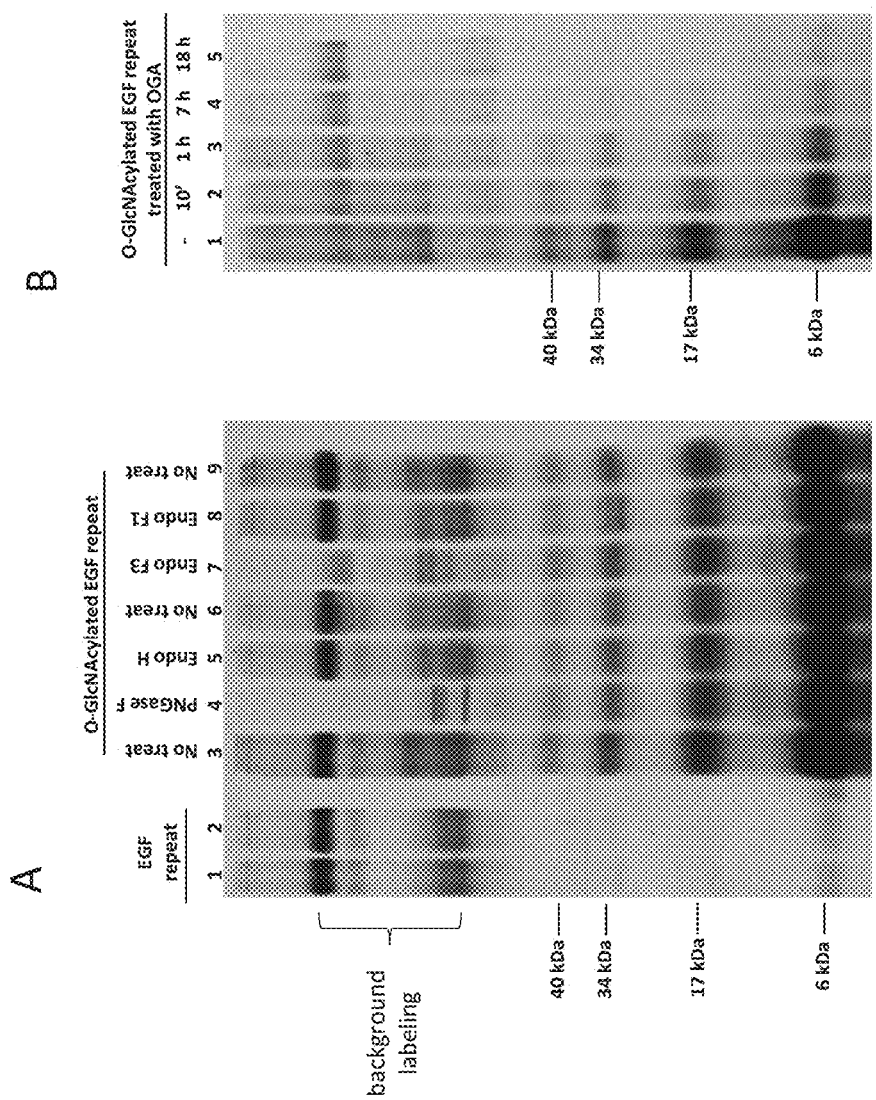
FIGS. 5A and 5B are autoradiographic images of samples resolved by gel electrophoresis showing $^{35}S$ sulfation of O-GlcNAc glycosylated EGF repeat labeled by CHST2.

The results of Examples 1, 3, 5, 6 and 7 (the results of which are shown in FIGS. 2, 3, 5, 6 and 7) were analyzed by electrophoresis. In Examples 1 and 3 (the results of which are shown in FIGS. 2 and 3), sulfated GlcNAc and O-GlcNAc peptide were separated on 8% SDS-PAGE in a running buffer of 40 mM Tris, pH 8.0 for 30 minutes according to the method described by Wu, Z. L., et al. (2010), 'A versatile polyacrylamide gel electrophoresis based sulfotransferase assay', *BMC Biotechnol*, 10, 11. In Examples 5, 6 and 7 (the results of which are shown in FIGS. 5, 6 and 7), sulfated O-GlcNAc glycosylated EGF domain repeat and cell extracts were separated on 12% SDS-PAGE for normal protein separation using the same method. After electrophoresis, gels were transferred to cellulose chromatography paper (Fisher Scientific, Cat#05714-1) and dried with a gel dryer at 80° C. under vacuum. The dried gels were then exposed to X-ray films for at least 30 minutes.

Example 1

The sulfotransferases CHST2 and CHST4 have been demonstrated to be active on oligosaccharides with different reducing end monosaccharides, including GlcNAcβ1-6Man, GlcNAcβ1-2Man and GlcNAcβ1-3Gal, as described by Uchimura, K., et al. (2002), 'Specificities of N-acetylglucosamine-6-O-sulfotransferases in relation to L-selectin ligand synthesis and tumor-associated enzyme expression', *J Biol Chem*, 277 (6), 3979-84. It was hypothesized that these enzymes are active on GlcNAc as well. This hypothesis was tested using an electrophoresis-based sulfotransferase assay as described in Wu et al. 2010.

A series of reactions were performed by combining 0.5 μl of either CHST2 or CHST4 with highly radioactive ($10^7$ cpm) $PAP^{35}S$ and one of a series of GlcNAc concentrations (in a five-fold serial dilution from 400 μM to 5.1 pM). The reactions were incubated at 37° C. for 4 hours and then resolved with 8% SDS-PAGE in lanes 1-8 using electrophoresis as described above. A control sample including only $PAP^{35}S$ was also run on lane 9.

The results are shown in FIGS. 2 A and B, which shows photographs of the exposed X-ray films. The samples shown in FIG. 2A included CHST2 while those in FIG. 2B included CHST4. The reaction in columns 1 had the highest concentration of GlcNAc, with decreasing concentrations in columns 2-8 and no GlcNAc in the control in columns 9 of each gel. The band representing the labeled sulfated GlcNAc, identified as GlcNAc6S in the figures, decreases in intensity as the concentration of GlcNAc decreases from columns 1 to 8 and is absent from column 9. The other bands which appear on the gels include excess $PAP^{35}S$, which is most intense in column 9, and free $^{35}SO_4^{2-}$ in columns 1-9. In FIG. 2A, a band of self-labeled CHST2 is also present at the top of columns 1-8, and absent from column 9 (which did not include CHST2). Self-labeling of CHST4 did not occur and hence there is no self-labeled band present in FIG. 2B.

Example 2

In this example, the Michaelis Menten constants of the two enzymes, CHST2 and CHST4, on GlcNAc were determined using a phosphatase-coupled sulfotransferase assay as described by Prather et al., 2012. The parameters were measured at constant concentration of PAPS of 0.36 mM at room temperature. The results are shown in Table 1, below, which shows the kinetics of CHST2 and CHST4 on GlcNAc. It is noted that CHST2 also catalyzed the addition of sulfate to itself, presumably through its N-glycans. Comparing the two enzymes, CHST4 was more specific on GlcNAc with a lower $K_m$ and a higher $V_{max}$.

TABLE 1

|  | $K_m$ (mM) | $V_{max}$ (pmol/min/μg) |
|---|---|---|
| CHST2 | 3.1 | 59.9 |
| CHST4 | 1.2 | 315 |

Example 3

In this example, the method was applied to the sulfation of O-GlcNAc peptide using an artificial O-GlcNAc peptide with CHST4.

Various concentrations of the O-GlcNAc peptide were reacted with CHST4 and $PAP^{35}S$ as described above. These were used in lanes 2, 3, 4 and 8 of an 8% SDS PAGE gel, for which 0.1, 0.2, 0.4 and 0.4 nmol O-GlcNAc peptide were used, respectively. In another reaction, 0.4 nmol of O-GlcNAc peptide was incubated with 0.2 μg OGA in 50 μL of a buffer containing 50 mM NaAc at pH 5.5 for 10 minutes at 37° C. to remove the O-GlcNAc from the peptide. The sample was then combined with CHST4 and $PAP^{35}S$, and this sample was used in lane 5 of the gel. For purposes of comparison, 2.5 nmol of GlcNAc, CHST4 and $PAP^{35}S$ were combined and this sample was used in lane 6. As a further comparison, 0.4 nmol of phosphopeptide, CHST4 and $PAP^{35}S$ were combined and this sample was run in lane 7. Finally, a sample containing only $PAP^{35}S$ was used in lanes 1 and 9. Electrophoresis was performed as described above and a photograph of the X-ray is shown in FIG. 3.

As can be seen in lanes 2, 3, 4, and 8 of FIG. 3, CHST4 introduced sulfate to the O-GlcNAc peptide. In lane 5, pretreatment of the O-GlcNAc peptide with OGA, a glycosidase that specifically removes O-GlcNAc, shifted the sulfated band to a position corresponding to sulfated GlcNAc. This band corresponds to the sulfated GlcNAc band in lane 6. In addition, when the phosphopeptide was used in lane 7 (in which a phosphate was present on the peptide in place of the O-GlcNAc) labeling was completely abolished, further demonstrating that the sulfation was on the O-GlcNAc residue. Excess $PAP^{35}S$ and free $^{35}SO_4^{2-}$ due to $PAP^{35}S$ degradation can be seen in all lanes.

Example 4

In this example, sulfation of the O-GlcNAc peptide was confirmed using a highly sensitive method of mass spectrometry. Sulfation reactions were performed by mixing 1 nmol O-GlcNAc peptide with either 5 nmol of PAPS or $PAP^{34}S$ and 1 μg CHST4 in 50 μL of a buffer of 25 mM Tris, pH 7.5, and incubated at room temperature for 1 hour. The labeled samples were then analyzed using LC-MS method for glycopeptide analysis as previously described by Leymarie and Zaia, 2012. The mass spectrometry results for the sample created using PAPS is shown in FIG. 4A, while FIG. 4B shows the results for the sample created using $PAP^{34}S$. Both samples produced a large peak at about 1116.55 representing the O-GlcNAc peptide. However, the peak representing the sulfated O-GlcNAc peptide is shifted by 1.9961 mas units greater, or about 2.000 units) when the sulfation was provided by $^{34}S$ in FIG. 4B as compared to $^{32}S$ in FIG. 4A. This shift correlates to the expected difference between $^{32}S$ and $^{34}S$ and confirms the correct identification of the peak as representing sulfated O-GlcNAc peptide and further confirms that sulfation of the O-GlcNAc peptide did indeed occur.

Example 5

In this example, the method was applied to the sulfation of a protein, a recombinant EGF domain repeat. The EGF domain repeat was first O-GlcNAcylated by mixing 40 μg EGF20, 5 μg EOGT, 1 μg CD39L3, and 1 mM UDP-GlcNAc in 600 μL reaction buffer (25 mM Tris, 0.15 M NaCl, pH 7.5) and incubating the mixture at 37° C. overnight. The CD39L3 was used in this reaction to remove the byproduct UDP to increase O-GlcNAcylation. A control reaction containing the same components except EOGT was also run side by side. Both the reaction and control mixtures were then dialyzed in reaction buffer overnight to remove UDP-GlcNAc.

The O-GlcNAcylated EGF repeat was then used in sulfation reactions by mixing 2 μg O-GlcNAcylated EGF repeat, 0.5 μg CHST2, and 5 μL PAP$^{35}$S (>$10^7$ CPM) in 15 μL total volume. Additional reactions were performed by combining all of the sulfated O-GlcNAcylated EGF with 0.2 μg of either PNGase F, Endo H, Endo F3, Endo F1, or OGA. A separate reaction was also performed, mixing 2 μg of EGF repeat with 0.5 μg CHST2, and 5 μL PAP$^{35}$S (>$10^7$ CPM). The reactions were resolved on 12% SDS PAGE under non-reducing conditions. Photographs of the autoradiographs of the resulting gels are shown in FIGS. 5A and 5B.

Samples from the reactions including O-GlcNAcylated EGF were used in lanes 3-9 of FIG. 5A. Of these, the reactions in lanes 3, 6, and 9 were not further treated with any glycosidase while lanes 4, 5, 7, and 8 were further treated with PNGase F, Endo H, Endo F3 and Endo F1, respectively. The unmodified EGF repeat was used in lanes 1 and 2. In lanes 1 and 2, in which unmodified EGF repeat was used as a substrate, there are bands due to background labeling, likely CHST2 self-labeling. In contrast, in lanes 3-9, in which O-GlcNAcylated EGF domain repeat was used as a substrate, several faster moving bands appeared.

In lanes 3 to 9 of FIG. 5A, there are four bands having molecular weight of 6, 17, 34 and 40 kDa. The use of PNGase F (lane 4), Endo H (lane 5), Endo F1 (lane 8) and Endo F3 (lane 7) had no effect on these fast moving bands, but only affected the bands corresponding to background labeling. This suggests that the background labeling was on N-glycans and the labeling of the faster moving bands was on O-glycans. This was further confirmed by treatment of O-GlcNAcylated EGF domain repeat with OGA, shown in lanes 1-5 of FIG. 5B after progressively more time of treatment. It can be seen that the use of OGA effectively reduced the intensities of the fast moving bands but left the bands due to background labeling unchanged.

These observations strongly suggest that sulfation of O-GlcNAc EGF domain repeat occurred on the O-GlcNAc residues. In addition, it can be seen that PNGase F was the best glycosidase for removing background labeling from FIG. 5A. However, Endo F3 was used in FIG. 5B for better demonstration that N-glycan was not removed by OGA treatment.

Example 6

In this example, labeling was performed with in vivo proteins using nuclear and cytoplasmic extracts from HEK293 cells from human embryonic kidney. (Graham et al. 1977)

The cell extract was prepared using HEK293 cells grown overnight in a 10 cm dish in IMDM media supplemented with 5% FBS (fetal bovine serum) at 37° C. with 5% of $CO_2$. $1\times10^7$ cells were harvested using 5 mL of fresh cold PBS (phosphate buffered saline) and centrifuged for 5 minutes at 450×g. The cell pellet was gently suspended using 600 μL of isotonic lysis buffer of 10 mM Tris-HCl 7.5, 2 mM $MgCl_2$, 3 mM $CaCl_2$, 0.3 M Sucrose, 0.2 mM PMSF (phenylmethylsulfonyl fluoride), and 0.5 mM DTT (dithiothreitol), and incubated for 15 minutes on ice. After centrifugation for 5 min at 420×g, the pellet was suspended with 150 μL of isotonic lysis buffer. The cells were then slowly passed through a syringe with a 27 gauge needle 6 times. The whole lysate was centrifuged for 20 min at 11,000×g and the supernatant was collected and used as the cytoplasmic extract for samples used in this example. The pellet was briefly washed with isotonic lysis buffer and then extracted using 150 μL extraction buffer (10 mM HEPES, pH 7.9, 1.5 mM $MgCl_2$, 0.2 mM EDTA (ethylenediaminetetraacetic acid), 25% Glycerol, 0.42 M NaCl, 0.2 mM PMSF, and 0.5 mM DTT). The lysate was occasionally vortexed and incubated on ice for 30 min. The supernatant was harvested after centrifugation at 21,000×g for 5 min and was used as the nuclear extract for the samples used in this example. Extracts were stored at −80° C.

For the results shown in FIG. 6A, nuclear extract and cytoplasmic extract were either directly labeled with CHST2 (lane 1, 2, 3 for nuclear extract and lane 6,7 for cytoplasmic extract) or labeled with CHST2 after OGA pretreatment (lane 4, 5 for OGA treated nuclear extract). A control reaction containing PAPS and CHST2 only was prepared and used in lane 8. Another control reaction containing PAPS and CHST2 and further treated with PNGase F was shown in lane 9 and 10. The samples were sulfated by combining all components in 25 μL with 0.5 μg recombinant human CHST2 and incubating at 37° C. for 20 minutes.

Reactions including the nuclear extract were prepared by combining 2, 4, or 8 μg of nuclear extract of HEK293 cells with 0.5 μg CHST2.

All reactions, except for one control, were further treated with PNGase F to remove the background labeling on N-glycans. For all reactions, samples were resolved on 12% SDS-PAGE under reducing conditions. Photographs of the results are shown in FIGS. 6A and 6B.

In FIG. 6A, the samples used in lanes 1, 2, and 3 contained 2, 4, and 8 μg of nuclear extract, respectively, without OGA. The samples used in lanes 4 and 5, by comparison, contained 4 and 8 μg of nuclear extract, respectively, with OGA treatment. By comparing lanes 1-3 with lanes 4-5, it can be seen that CHST2 labeling was sensitive to OGA treatment. The samples used in lanes 6 and 7 contained 4 and 8 μg of cytoplasmic extract, respectively, without OGA. The samples used in lanes 8-10, the control lanes, included no extract. All other reactions were further treated with PNGase F to remove the background labeling on N-glycans except for the reaction used in lane 8, for which no PNGase F was used.

Figure 4:
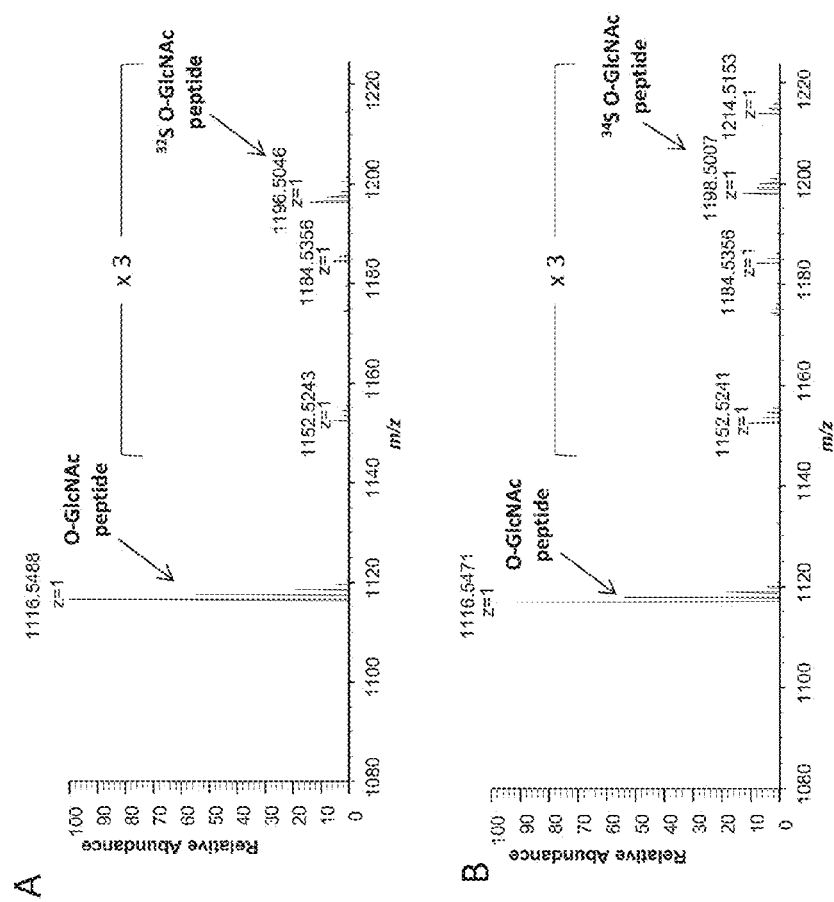
FIGS. 4A and 4B are mass spectroscopy results for O-GlcNAc glycosylated peptide sulfated by CHST4 using $PAP^{32}S$ (FIG. 4A) and $PAP^{34}S$ (FIG. 4B).

In lanes 1-3 of FIG. 6B, 4 μg nuclear extract was used in each reaction, while in lanes 4-6, 4 μg cytoplasmic extract was used in each reaction. For comparison, OGA and OGT treated samples were done simultaneously as well. When the nuclear extract and cytoplasmic extract of HEK293 cells were pretreated with OGA as shown in lanes 2 and 5, respectively, the labeling was significantly reduced. In contrast, when the samples were pretreated with OGT as shown in lanes 3 and 6, some bands on the gel were intensified. In addition, three novel bands, indicated by arrows, only appeared in OGT treated samples. This suggests that O-GlcNAcylation sites on these proteins were almost completely unoccupied in vivo.

Example 7

In this example, labeling of nuclear extract using CHST2 and CHST4 were compared side by side. The nuclear extract of HEK293 cells was prepared as described above. In each reaction, nuclear extract (except in the controls) was combined with 0.5 μg CHST4 or CHST2, $10\times10^7$ CPM of PAP$^{35}$S, and 0.2 μg of PNGase F to remove background labeling, and in some cases the samples were pretreated with 0.2 μg OGA. When OGA was used, the samples were pretreated with OGA for 10 minutes before labeling. All reactions were resolved on 12% SDS-PAGE under reducing conditions. A photograph of the results is shown in FIG. 7.

In lanes 1-6 of FIG. 7, the reactions included CHST4, while in lanes 8-13, the reactions included CHST2. In lanes 1, 4, 8, and 11, 1 μg of nuclear extract was used in the reaction. In lanes 2, 5, 9, and 12, 2 μg of nuclear extract was used in the reaction. In lanes 3, 6, 10, and 13, 4 μg of nuclear extract was used. Lanes 7 and 14 included no nuclear extract and were used as controls to show the background labeling. While the majority of the labeled bands were similar in both cases, some bands were more significant in one labeling than the other, suggesting that the two enzymes vary slightly in their substrate preferences.

The invention claimed is:

1. A method of detecting the presence of O-GlcNAc (O-linked β-N-acetvlglucosamine) modification of a peptide or protein comprising sequential steps of:
    a) combining the peptide or protein with EOGT (extracellular O-GlcNAc transferase) or OGT (O-GlcNAc transferase) and UDP-GlcNAc (Uridine 5'-diphospho-N-acetylglucosamine) to produce a first reaction product;
    b) combining the first reaction product with PAP$^{35}$S (3'-Phosphoadenosine-5'-phosphate including $^{35}$S) and a sulfotransferase to produce a second reaction product including $^{35}$S labeled O-GlcNAc modified peptide or protein;
    c) removing background labeling with a glycosidase;
    d) separating the $^{35}$S labeled O-GlcNAc modified peptide or protein from PAP$^{35}$S, free $^{35}$S sulfate and labeled oligosaccharides if present; and
    e) detecting isotopic emissions from the $^{35}$S labeled O-GlcNAc modified peptide or protein.

2. The method of claim 1 wherein the sulfotransferase comprises CHST2 (N-acetylglucosamine 6-O-sulfotransferase 1) or CHST4 (N-acetylglucosamine 6-O-sulfotransferase 2).

3. The method of claim 2 wherein step d) comprises resolving the second reaction product in gel using gel electrophoresis.

4. The method of claim 3 wherein step e) comprises producing a radiograph of the gel and identifying a band corresponding to O-GlcNAc modified peptide or protein.

5. The method of claim 4 further comprising:
    f) scanning the radiograph and detecting the density of a band corresponding to the $^{35}$S labeled O-GlcNAc modified peptide or protein.

6. The method of claim 3 wherein step e) comprises detecting isotopic emissions from the gel using a phosphorimager.

7. The method of claim 2 wherein step d) comprises passing the second reaction product through a desalting column and wherein step e) comprises counting radioactive emission of the $^{35}$S labeled O-GlcNAc modified peptide or protein using a liquid scintillation counter.

8. The method of claim 2 wherein step d) comprises applying the second reaction product to a filter having an affinity for peptide or protein and wherein step e) comprises counting radioactive emission of the $^{35}$S labeled O-GlcNAc modified peptide or protein using a liquid scintillation counter.

9. The method of claim 2 wherein step d) comprises binding the $^{35}$S labeled O-GlcNAc modified peptide or protein using antibody specific to the $^{35}$S labeled O-GlcNAc modified peptide or protein, forming an immunoprecipitate, and separating out the immunoprecitipate and wherein step e) comprises counting radioactive emission of the $^{35}$S labeled O-GlcNAc modified peptide or protein using a liquid scintillation counter.

10. The method of claim 1 further comprising combining the peptide or protein with CD39L3 (ectonucleoside triphosphate diphosphohydrolase-3) at the same time as combining the peptide or protein with EOGT or OGT and UDP-GlcNAc.

11. The method of claim 1 further comprising combining the second reaction product of step b) with IMPAD1 (inositol monophosphatase 3).

12. The method of claim 1 wherein in step c) the glycosidase comprises PNGase F.

\* \* \* \* \*